US009319636B2

(12) United States Patent
King

(10) Patent No.: US 9,319,636 B2
(45) Date of Patent: Apr. 19, 2016

(54) VIDEO IMAGING SYSTEM WITH MULTIPLE CAMERA WHITE BALANCE CAPABILITY

(71) Applicant: Karl Storz Imaging, Inc., Goleta, CA (US)

(72) Inventor: Timothy King, Goleta, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 197 days.

(21) Appl. No.: 13/731,159

(22) Filed: Dec. 31, 2012

(65) Prior Publication Data

US 2014/0184765 A1    Jul. 3, 2014

(51) Int. Cl.
| | | |
|---|---|---|
| A62B 1/04 | (2006.01) |
| H04N 7/18 | (2006.01) |
| H04N 9/73 | (2006.01) |
| A61B 1/045 | (2006.01) |
| A61B 1/00 | (2006.01) |
| A61B 1/04 | (2006.01) |
| A61B 1/05 | (2006.01) |

(52) U.S. Cl.
CPC .............. *H04N 7/18* (2013.01); *A61B 1/00009* (2013.01); *A61B 1/00057* (2013.01); *A61B 1/00059* (2013.01); *A61B 1/042* (2013.01); *A61B 1/045* (2013.01); *A61B 1/053* (2013.01); *H04N 9/735* (2013.01)

(58) Field of Classification Search
CPC ............ H04N 9/73; H04N 7/18; H04N 9/735
USPC .......................................................... 348/65
See application file for complete search history.

(56) References Cited

U.S. PATENT DOCUMENTS

| | | | |
|---|---|---|---|
| 3,627,911 A * | 12/1971 | Kubota et al. ............... 348/228.1 |
| 3,971,068 A * | 7/1976 | Gerhardt ................ G01R 13/22 |
| | | | 348/E9.028 |
| 4,816,909 A | 3/1989 | Kimura et al. |
| 4,831,437 A | 5/1989 | Nishioka et al. |
| 5,570,129 A | 10/1996 | Hafele et al. |
| 5,685,821 A | 11/1997 | Pike |
| 6,315,712 B1 | 11/2001 | Rovegno |
| 6,421,070 B1 | 7/2002 | Ramos et al. |
| 6,638,212 B1 | 10/2003 | Oshima |
| 6,943,822 B2 | 9/2005 | Iida et al. |
| 6,976,954 B2 | 12/2005 | Takahashi |
| 7,167,196 B2 | 1/2007 | Saito et al. |
| 7,453,490 B2 | 11/2008 | Gunday |
| 2005/0046703 A1* | 3/2005 | Cutler ......................... 348/223.1 |
| 2005/0093997 A1* | 5/2005 | Dalton et al. ............... 348/227.1 |
| 2006/0055793 A1* | 3/2006 | Adler et al. ............... 348/211.99 |

(Continued)

*Primary Examiner* — Leron Beck
(74) *Attorney, Agent, or Firm* — Whitmyer IP Group LLC

(57) ABSTRACT

A system for capturing image data including a control module having a control switch and a processor, the processor being adapted for white balance control and the control switch being adapted to initiate white balance control, at least one input module connected to the control module, the input module providing white balance calibration, and at least one camera coupled to the input module. One or more of the at least one input module are configured as active input modules, each active input module having an active camera generating an image signal. The control module detects the one or more active input modules and controls one of the one or more active input modules, selected based on user feedback, to calibrate white balance of the image signal of the active camera coupled to the selected input module and to transmit the calibrated image signal to the control module for display.

33 Claims, 4 Drawing Sheets

(56) References Cited

U.S. PATENT DOCUMENTS

| | | | |
|---|---|---|---|
| 2007/0024717 A1* | 2/2007 | Chatenever et al. | 348/211.99 |
| 2007/0123749 A1* | 5/2007 | Iwasaki et al. | 600/117 |
| 2009/0033786 A1* | 2/2009 | Finkelstein | G02B 7/285 348/345 |
| 2009/0096895 A1* | 4/2009 | Benezra | H04N 9/735 348/234 |
| 2010/0069711 A1* | 3/2010 | Deng et al. | 600/104 |
| 2010/0077431 A1* | 3/2010 | Neufeld et al. | 725/39 |
| 2013/0235178 A1* | 9/2013 | Wang | H04N 5/33 348/77 |

* cited by examiner

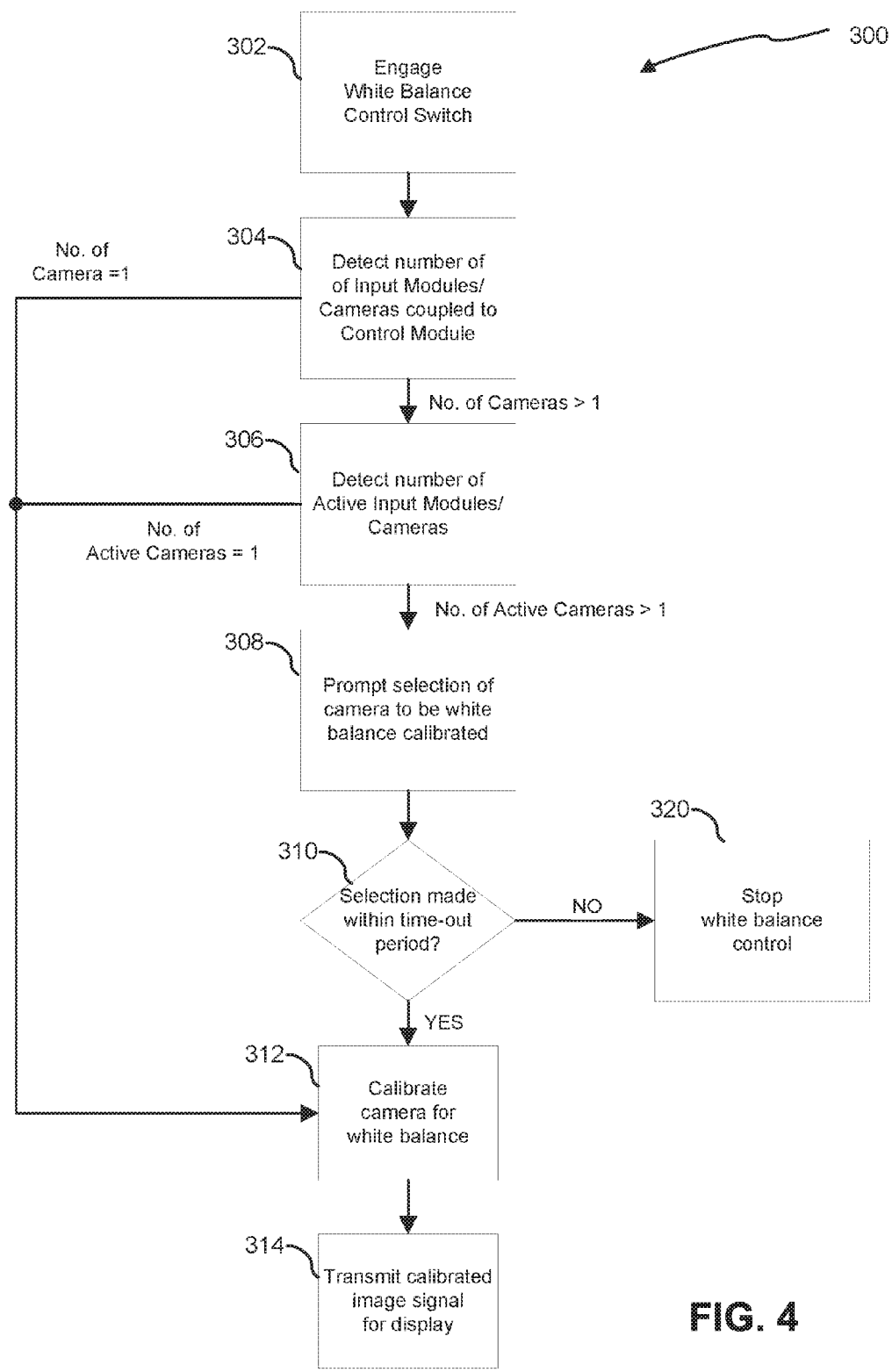

VIDEO IMAGING SYSTEM WITH MULTIPLE CAMERA WHITE BALANCE CAPABILITY

FIELD OF THE INVENTION

This invention relates to a video imaging system for processing image signals from a plurality of cameras, and more particularly, a modular image capturing system having a white balance capability for calibrating white balance of multiple cameras having identical and/or different make and imaging architecture.

BACKGROUND OF THE INVENTION

The field of endoscopy, to which the present invention relates, includes medical diagnostic and therapeutic disciplines that utilize endoscopes to view otherwise inaccessible body cavities using minimally invasive surgical procedures. Endoscopic cameras are typically small and lightweight for ease of use by medical professionals. Typically, the camera is connected to a Camera Control Unit ("CCU"), with the CCU processing and displaying image data from the camera. Often, each medical procedure requires a different camera having different imaging capabilities, leading to a large inventory of cameras. Additionally, each camera must be compatible with the CCU to function correctly.

In known systems, cameras, such as charge coupled devices and the like, used during endoscopic surgery are typically referred to as heads or camera heads. To achieve the desired size and weight of the camera heads, camera head and/or integrated endoscope-camera assembly electronics are typically separated physically from the majority of circuitry required to process and output high-quality, color video images, which is typically housed in the CCU. In known systems, CCUs may be placed on or in carts, or may be permanently wall-mounted.

When image data is acquired, or picked up, it is sent by the camera head to the CCU. Upon receiving the image data from the camera head, the CCU normally processes the signal to display the acquired image on a viewing device. Generally, the image is used by a medical professional and/or for storage on various media (video cassette recorder, floppy disk, hard drives, flash drives, compact disks, digital video disks, and the like) and/or for transmission to remote locations in various manners, such as by the Intranet, Internet, radio transmission, and the like.

Additionally, the CCU may send commands to the camera head to adjust various settings, such as electronic shutter for light sensitivity, and other optical and electronic characteristics.

It is known to provide a CCU that, at any one time, is capable of supporting one of a limited number of compatible camera heads, where each camera head may have different settings and a distinct image signal format. For example, each camera head may have its own unique white balance calibration requirements and settings. White balance includes the process of removing unrealistic color casts, performing color correction, and establishing color fidelity so that objects which appear white in person are rendered white in the image or video. In the medical field, maintaining color fidelity in the camera head and CCU is important because medical professionals routinely make diagnostic decisions based on the appearance, i.e. color, of anatomical structures. Therefore, if a camera's white balance is not properly set, the resulting diagnosis made by the medical professional using the camera may be incorrect and cause adverse, and at times catastrophic, consequences for the patient.

For a conventional CCU having a single camera head coupled thereto, "white balancing" the head is performed prior to the start of a medical procedure. This process requires that the medical professional hold the camera head, aim the camera's objective lens and corresponding light source towards a white surface (e.g., white gauze, white balance card) such that the camera's field of view is filled by the white surface, and engage a control button on the CCU or on the camera head to start white balancing the camera head.

However, conventional CCUs suffer from several disadvantages with respect to their white balance capability. For example, conventional CCUs fail to provide efficient and secure means for white balancing multiple camera heads that are coupled to the control unit. Moreover, the CCUs fail to provide efficient and reliable means for white balancing a select group of camera heads from among a plurality of camera heads coupled to the control unit. Some CCUs which have a limited number of camera heads are configured with multiple white balance calibration buttons, each button being designated to calibrate a specific camera head. However, with such a setup, there is often no easy or readily apparent way to tell which calibration button is linked to which camera. Accordingly, a medical professional may accidentally and unknowingly calibrate the wrong camera and use an uncalibrated camera during a medical procedure. In order to avoid making this mistake, the medical professional would have to take time to trace the transmission cable connecting a selected camera back to the CCU from among multiple transmission cables connecting other cameras to the CCU. This tedious task may further be complicated if the transmission cables are coupled to the CCU via a rear connection panel that is not easily accessible.

A conventional CCU is also unable to efficiently and properly determine from a group of active camera heads a specific camera to white balance. With multiple image signals being transmitted from the active camera heads, the CCU is unable to reconcile which camera head (i.e., the camera which the medical professional plans to use) must be calibrated for white balance. Instead of trying to trace a particular camera head back to the CCU to determine the correct white balance calibration button to engage, the medical professional may calibrate all the camera heads coupled to the CCU in order to prevent the potential for misdiagnosis due to use of an uncalibrated camera head. However, calibrating all cameras coupled to the CCU takes additional time that is unnecessary when the medical professional requires use of only one specific camera for a given medical procedure.

Other conventional CCUs may not incorporate or have an integrated white balance functionality. As an alternative, each camera head attached to the CCU is equipped with its own calibration button. However, this particular CCU-camera configuration has its own disadvantages. The CCUs often lack the capacity to deactivate the white balance calibration buttons on the camera heads. As such, there is the possibility that the medical professional may accidentally engage the calibration button while the camera head is in use, i.e., inserted within a patient. Calibrating the camera head while it is disposed within a body cavity will establish a distorted color balance setting and provide defective color fidelity in the image signal. The medical professional would have to cease the surgical operation, remove the endoscope-camera from the patient, repeat white balance calibration of the camera (pointing the camera at a white surface to form a baseline for calibration), carefully reinsert the endoscope to its previous position within the incision and cavity made within the patient, and thereafter continue with the surgical operation. Accordingly, the medical professional must stop the surgical operation for a significant downtime to correct the accidental calibration of the camera head.

Another disadvantage which conventional CCUs have is their inability to provide dual white balance for multiple camera heads coupled to the CCU, wherein the camera heads have multi-spectral imaging capability (i.e., wide band imaging and narrow band imaging) and/or comprises different light source technology. More specifically, prior art CCUs often do not provide color correction for multiple camera heads having different light sources, such as white light cystoscopic cameras and blue light photodynamic diagnostic (PDD) cystoscopic cameras. An extended color balance range is required in order to correctly calibrate PDD cameras for color fidelity compared to typical white light cameras. Conventional CCUs are unable to detect or distinguish the different cameras and often lack the technology and capability to perform dual white balance (white balance for both white light and blue imaging technology).

Further, conventional CCUs do not have the capability to perform dual white balance on a plurality of active camera heads such that the images from different camera heads have matching picture quality and characteristics (e.g., color balance, hue, saturation, contrast, brightness).

It is further noted that conventional CCUs often lack the capability to function with multiple cameras/video endoscopes having diverse types of imaging technology (e.g., CCD sensors, analog CMOS sensors, digital CMOS sensors) and distinct white balance calibration requirements. Often, such cameras do not work well together when connected to a common CCU. Typically, conventional CCUs are designed so that they are compatible only with a particular family of camera heads having the same imaging design and white balance calibration requirements.

In light of several disadvantages of conventional CCUs, it is therefore desired to overcome these disadvantages and provide an imaging system that can function with a plurality of camera heads, efficiently calibrate the white balance of all active camera heads, and protect their white balance settings from unintentional adjustments. It is also desired to provide a CCU that can perform dual white balance calibration on one or more multi-spectral imaging camera heads coupled thereto. Further, it is desired to provide a CCU that is capable of calibrating the white balance of more than one active camera such that a common image quality may be achieved among the cameras.

SUMMARY OF THE INVENTION

Accordingly, it is an object of the present invention to remedy the problems of conventional CCUs, which fail to provide efficient white balance calibration for one or more active camera heads coupled to the control unit. The present invention provides an image capturing system and method that allows for efficient and reliable white balance correction of one or more active cameras, to be used in a medical procedure, from among a plurality of cameras coupled to the image capturing system.

It is a further object to provide an image capturing system, and related method, having a controller that provides dual white balance compensation for one or more active cameras having multi-spectral imaging capabilities (e.g., wide band imaging and narrow band imaging) and/or different imaging/light source technology.

It is an additional object to provide an image capturing system having a controller which adjusts white balance settings of a plurality of active cameras to be used so that the image data transmitted from each active camera has matching color fidelity. As such, when the image data of each active camera is displayed, for example side by side, the image quality of the pictures looks the same to the user.

It is another object to provide an image capturing system which is adapted to calibrate dual white balance of one or more cameras that are activated (e.g., powered on) at a time after an initial white balance calibration of one or more active cameras so that the image quality of the newly activated camera matches the image quality of the active cameras. Often, there are times when a medical professional does not anticipate using a particular camera head for a medical procedure, but later determines, during the procedure, that the particular camera head is needed and thus must be activated and calibrated.

It is a further object to provide an image capturing system which provides safeguards against unintentional calibration of white balance of a camera head that is being used during a medical procedure, i.e., a camera head or an endoscopic instrument connected to the camera head inserted within a patient's body.

It is also an object of the present invention to provide an image capturing system wherein image acquisition, processing, and display are segmented in such a manner as to optimize adaptability and compatibility with existing and future camera/image sensor technology, formats and architectures, as well as with existing and future display technologies.

These and other objectives are achieved by providing a system and method for capturing image data and color correcting the image data by adjusting the white balance of multiple camera heads coupled to the system, in order to display images with matching color balance and color fidelity. In particular, these and other objectives are achieved by providing a system for capturing image data including a control module having a processor adapted for white balance control and a control switch adapted for initiating white balance control, and one or more input modules releasably connected to the control module, wherein at least one camera is coupleable to each input module. Once the control module and input modules are connected, communication is established between the input modules and the processor through a multiplexer. The control module is adapted to detect at least one active input module from among the one or more input modules, wherein the at least one active input module has one or more active cameras generating image signals. The control module controls one of the at least one active input module, selected based on user feedback, to calibrate the white balance of the image signals of the selected camera.

Noted herein, the terms "camera" and "camera heads" encompass all types of image and video capturing devices, including still cameras, video cameras, high-definition cameras, digital cameras, video endoscopes, and including imager architecture/design types such as charge-coupled device (CCD) image sensors, and complementary metal-oxide-semiconductor (CMOS) image sensors.

Also, the terms "color balance calibration," "color correction," "white balance compensation," and "color balance compensation" are used interchangeably herein with "white balance calibration" and are used to convey the same process of adjusting the intensity of colors and rending neutral colors correctly within an image.

Further, the image capturing system with its modular design of one control module releasably connected to one or more input modules is adapted to provide white balance capability that supports a plurality of cameras having identical and/or different imaging architecture. Each input module may be configured and designed to be compatible with a family of cameras, where all the cameras of the family have a common imaging architecture. Accordingly, the input modules function also as communication interfaces so that data generated by diverse cameras may be interpreted and processed by the control module.

In some embodiments, the one or more input modules are adapted with dual white balance function. The input modules can therefore provide proper color compensation for cameras comprising different imaging/light source technology (e.g., white light, blue light). More specifically, the control module may control the active input modules to calibrate each image signal so that color compensation accounts for different light sources. This is advantageous since some camera heads are designed to utilize blue light imaging for obtaining more detailed images while other camera heads are designed using conventional white light imaging; further yet, some cameras are configurable to provide either type of imaging. Dual white balance provides for automatic regulation of camera color control so as to match the camera color to the color temperature of the specific light source used. The image signals/data transmitted to the control module from the active input modules, in turn, exhibit a color balance that accurately represents natural lighting conditions. This aids in maintaining color fidelity, which is important for a medical professional using the image capturing system to correctly diagnose a patient.

Further objectives are achieved by providing an image capturing system having a control module with a processor and a white balance control switch, at least one input module connected to the control module, and at least one camera coupled to the at least one input module, wherein the control module controls one of the at least one input module, selected by a user, to calibrate white balance of the image signal of a selected camera coupled to the selected input module and wherein the control module locks white balance calibration of the at least one input module so that calibration of the image signal of the selected camera may be initiated only through the control switch disposed on the control module. Any calibration button on the camera itself is deactivated.

In some embodiments, the selected input module retrieves camera information from the selected camera coupled to the selected input module and uses the camera information to properly calibrate the white balance of the image signal of the selected camera. The camera information which the input module may use to perform white balance calibration includes current image settings, imaging configuration data, and white balance requirements of the selected camera.

Other objectives are achieved by providing an image capturing system, which includes a control module having a control switch and a processor, the processor being adapted for white balance control and the control switch being adapted to initiate white balance control, at least one input module connected to the control module, the at least one input module providing white balance calibration, and at least one camera coupled to each of the at least one input module, wherein one or more of the at least one input module is configured as active input modules, each active input module having an active camera generating an image signal. The control module can detect at least two active input modules, each active input module having at least one active camera, wherein the control module controls at least two of the active input modules, selected based on user feedback, to calibrate white balance of the image signals of the selected cameras to have matching balance of color and color fidelity. As such, the image generated by one selected camera will exhibit color intensities that match those exhibited in the image generated by another selected camera. In other words, the images calibrated by the selected input modules will look substantially the same to the user.

The image capturing system is also designed to assist in calibrating white balance of one or more cameras that are activated at a later time after an initial white balance calibration has been performed on active cameras. In particular, the control module detects the newly activated camera head, controls the input module coupled to the newly activated camera head to perform white balance calibration on the image signal of the newly activated camera, and adjusts the white balance of the image signal so that the newly activated camera provides matching color fidelity as the prior-calibrated active cameras. This feature is beneficial because the medical professional does not have to cease use of the active cameras and recalibrate their white balance along with calibrating white balance of the newly activated camera to obtain a consistent color balance among all cameras (active cameras and newly activated camera). Therefore, an accurate and efficient means of white balance calibration is provided.

In some embodiments, the control module of the image capturing system is adapted to also adjust other image parameters to achieve an accurate and true color fidelity. For example, the control module, via the input modules, may adjust hue and saturation of the image signals. Contrast/brightness/intensity may also be adjusted. Furthermore, the control module is adapted to adjust these image parameters in order to achieve matching color fidelity between image signals of two or more selected cameras.

A storage unit may also be included with each of the input modules, wherein each storage unit saves the white balance calibration settings for each active camera coupled to the input module. The saved calibration settings may be used at a later time, or perhaps in a subsequent medical procedure, to quickly configure the white balance of the active cameras. This is particularly helpful where a user (i.e., medical professional) has specific personal preferences regarding white balance settings of certain cameras or video endoscopes. The amount of time for calibrating active cameras coupled to the image capturing system can be reduced by merely uploading the saved white balance calibration settings. Saving white balance calibration settings of the cameras on the storage unit is also beneficial if an active input module and/or active camera is inadvertently disconnected from the control module (or the communication/connection between the control module and the input module/camera fails) during a medical procedure. When the particular input module or camera is reconnected to the control module (or communication therebetween is re-established), the medical professional may use the saved calibration settings to quickly calibrate the white balance of the "fault" camera without having to remove it from a patient's body. Accordingly, the amount of downtime due to the connection failure can be minimized. The storage unit may also be adapted to save camera information (e.g., image settings, imaging configuration data, calibration requirements, the type/kind of camera) retrieved by the input module from the active camera(s) coupled thereto. In some embodiments, the storage unit is integrated with the input module as an internal storage unit. In other embodiments, the storage unit may be an external storage device that connects to the input module.

In some embodiments, at least one display monitor may be coupled to the control module for displaying the color corrected/calibrated image signals of the active cameras that are transmitted to the control module. The control module is adapted with multiple interface ports which provide for a variety of display monitors to be connected thereto.

Additional devices may be coupled with the control module. For example, a keyboard or keypad may be coupled to the control module for inputting data or adjusting settings of the control module, input modules, and/or cameras heads. The control module may also be adapted with network connectivity, such as Ethernet ports or wireless transmitter/receivers, so that image data may be transmitted to remote locations. In some embodiments, white balance calibration by the image capturing system may be initiated and observed remotely. For example, prior to the medical professional arriving at the operating room, he or she can observe the calibration process being performed by another person (e.g., nurse) from an office computer. Further, an external light source and/or insufflator may be coupleable with the control module to provide light and insufflation to the camera/endoscopic instrument. A storage device (e.g., external hard drive) may also be coupled to the control module to store the calibrated image signals transmitted to the control module. The storage device further saves the actual display view shown on the display monitor, wherein the display view may comprise the calibrated image signals enhanced by the control module (e.g., adjusted contrast levels, GUI overlay, PIP format).

Further objectives are achieved by providing a system for capturing image data which includes a control module having a processor, the processor being adapted for white balance control, and a plurality of input modules releasably connected to the control module and communicating with the processor, wherein each input module is compatible with a family of cameras where all cameras of the family have a common imaging design/architecture and wherein at least one compatible camera is coupled to each of the input modules. The control module is adapted to detect at least two active input modules each having at least one active camera, wherein each active camera generates an image signal transmitted to the control module. The control module is further adapted to receive user feedback regarding a selection of one camera from the group of active cameras to be calibrated. The control module then controls the active input module, that is coupled to the selected camera, to calibrate dual white balance of the image signal of the selected camera.

In some embodiments, the control module is adapted to receive user feedback about two or more cameras selected from the group of active cameras to be calibrated, and control the active image modules, that are coupled to the selected cameras, to calibrate dual white balance of the image signals of the selected cameras. As such, although there may initially be several active cameras coupled to the system, the user may select a subset of the active cameras to be color corrected, wherein the subset includes the cameras which the user intends to use during a surgical procedure.

Additional objectives are achieved by providing a method of capturing image data using an imaging system, wherein the method includes the steps of providing a control module and at least one input module, wherein the control module has a processor adapted for white balance control and a control switch adapted to initiate white balance control, connecting the at least one input module to the control module, and coupling at least one compatible camera to the at least one input module. The method also includes the step of detecting, via the control module, at least one active input module from among the at least one input module, the active input module having one or more active cameras, wherein each active camera generates an image signal, and selecting at least active camera for calibrating dual white balance. The method further comprises the steps of controlling, via the control module, the active input module that is coupled to the selected camera to calibrate dual white balance of the image signal of the selected camera, and transmitting the calibrated image signal from the selected camera to the control module for display on the display monitor.

Other features and aspects of the present invention will become more apparent from the following detailed description, taken in conjunction with the accompanying drawings, which illustrate by way of example, the features in accordance with embodiments of the invention. The summary is not intended to limit the scope of the invention, which is defined solely by the claims attached thereto.

BRIEF DESCRIPTION OF THE DRAWINGS

FIG. 4 is a flowchart of a method of calibrating white balance of a camera using the image capturing system of FIG. 1.

DETAILED DESCRIPTION OF THE INVENTION

Figure 1:
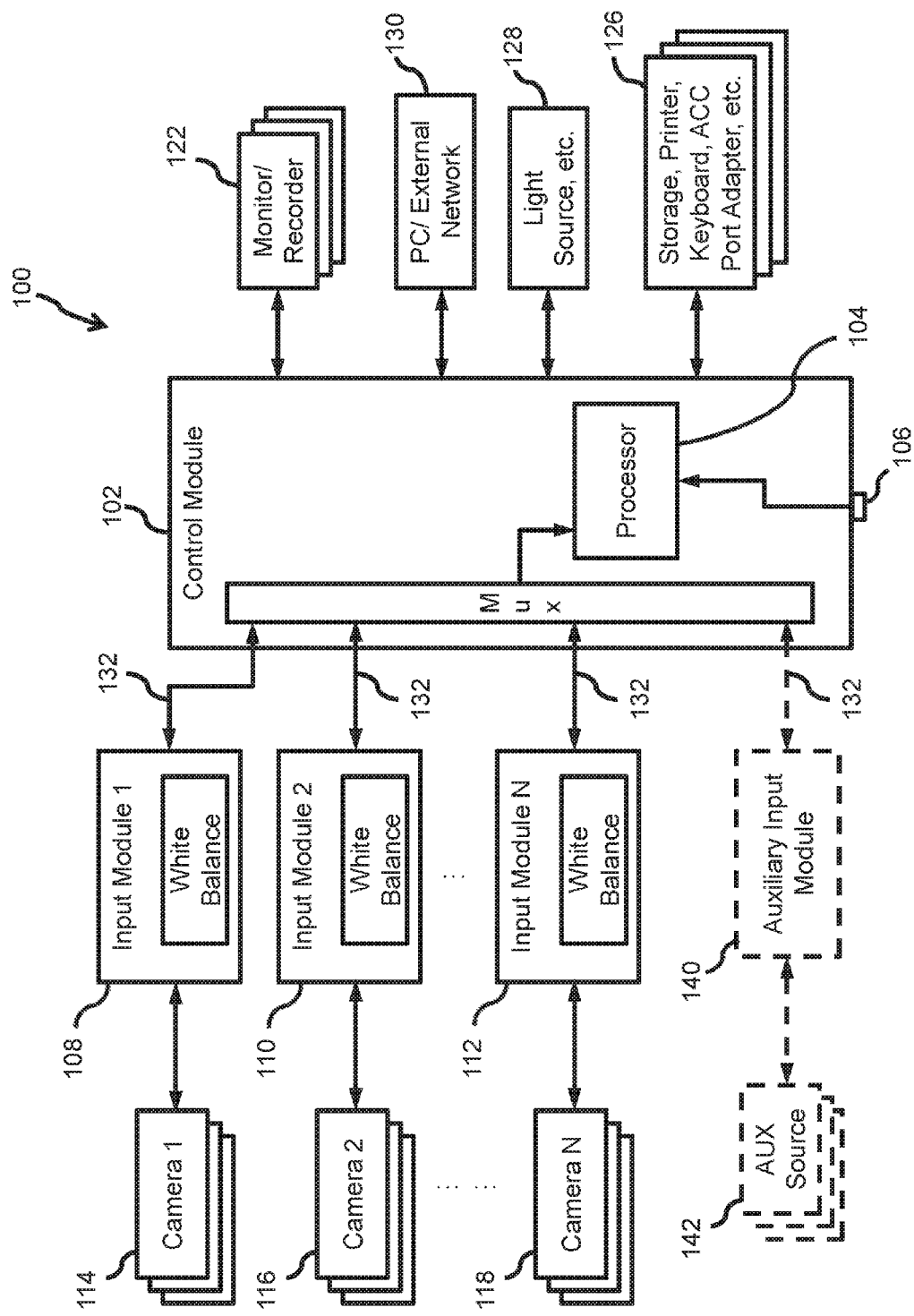
FIG. 1 is a block diagram of an image capturing system according to an exemplary embodiment of the present invention.

The following detailed description illustrates the invention by way of example, not by way of limitation of the principles of the invention.

As used herein, the terms "camera" and "camera heads" encompass all types of image and video capturing devices, including still cameras, video cameras, HD cameras, digital cameras, video endoscopes, and including imager architecture/design types such as CCD image sensors, and CMOS images sensors.

As used herein, the term "white balance calibration" encompasses (and is used interchangeably with) white balance compensation, color correction, color calibration, color balance calibration, and color balance compensation.

The present invention concerns an imaging system or image capturing system that is adapted to calibrate the white balance setting of one or more camera heads coupled to the system. More specifically, the image capturing system provides dual white balance compensation for multiple camera heads having multi-spectral imaging capability (e.g., wide band imaging and/or narrow band imaging). Further, the image capturing system is adapted to provide dual white balance calibration to a plurality of camera heads, wherein each camera head may have a different imaging design/architecture, including different light source technology.

To accommodate the growing variety of camera heads being developed, the image capturing system may be designed with a modular architecture. The modular system allows for increased flexibility for the consumer. The modular image capturing system allows upgradeability and compatibility with a multitude of camera heads that are supported by a plurality of input modules, where the camera heads and input modules may be existing or yet to be developed. Formerly, when a new imaging technology became available, a camera control unit could be incompatible with the new technology due to a variety of constraints, for example, hardware. By using a modular architecture, the new technology can be supported by an input module that is compatible with a control module of the imaging system. In order to streamline the flexibility of the modular architecture, it is important to have an efficient way to re-program or re-configure the modular imaging system software, firmware, drivers, etc. The modular architecture increases the likelihood that existing visualization technology and yet to be developed visualization will be able to operate with some if not all of the same image processing hardware. This results in decreased capital costs for physicians offices.

The control module of the image capturing system according to the present invention is designed to accommodate general image processing and display functions for multiple camera types or families. These general functions include, for example, user interface, image capture and streaming functionality as well as input/output functionality for the display/monitor interfaces, system interface and control, and network connectivity. The control module can be designed to accommodate one or multiple imaging modules.

In an example of a control module that supports only one input module at a time, the overall modular system can be purchased at a lower initial cost. If the consumer wishes to purchase different camera or input module types, the modular device may be re-programmed to work with different imaging technology. If the control module supports multiple input modules, the consumer may still purchase new imaging technology, cameras and/or input modules, and still use the same control module once any necessary re-programming is completed.

The input modules may support all functions required for a group or family of image sources, such as cameras. The input module provides compatibility between the family of image sources and the control module. Over the life of the system, additional input modules may be purchased to support emerging imaging technology such as 3D imaging, advanced fluorescence imaging, solid-state variable direction of view endoscopes, wireless camera heads and the like.

The group of input modules connected to the control module may include an auxiliary input module. The auxiliary input module supports a variety of video sources such as other camera control units, C-Arm, X-Ray, Ultrasound, Personal Computers and the like. Supported input formats may include DVI, VGA, S-Video, Composite, 3G-SDI and the like. Inputs may be both automatically and manually selected. The auxiliary input module provides increased backward compatibility, forward compatibility and third party image source compatibility.

The modular architecture provides an image capturing system wherein the image acquisition, processing, and display functionalities are segmented in such a manner as to optimize adaptability and compatibility with existing and future camera formats and architectures as well as with existing and future display technologies. The modular architecture, with a re-programmability architecture allows for economical buyers to progressively upgrade their imaging technology, rather than being required to purchase a camera control unit that is compatible with the entire range of imagers that the buyer would wish to purchase in the future. The efficient re-programmability function allows for hardware upgrades through input modules as well as software feature upgrades. The re-programmability function further minimizes the likelihood that newly purchased visualization technology will become obsolete while increasing backward compatibility of upgrades. Further, the cost of ownership and upgrade, such as acquisition, back-up, and maintenance, is reduced.

With the increased flexibility of the modular image capturing system relative to working with a variety of different camera heads and imaging technology, the system must also provide image calibrating and image enhancing capabilities that work properly and efficiently with each of the camera heads. One key characteristic of the cameras which should be managed and controlled by the modular image capturing system and, more specifically the control module of the system, is white balance. Each camera head of different make has its own unique white/color balance calibration requirements and data. Correct color balance calibration of each active camera head coupled to the system is important to ensure color fidelity of the images generated. If the camera heads are not calibrated or are calibrated incorrectly, a medical professional using the camera heads may misdiagnose a patient. Accordingly, an image capturing system is needed which is able to efficiently and properly calibrate white balance of a plurality of camera heads coupled thereto, wherein the cameras have different imaging and light source technology.

Referring now to the drawings, wherein like reference numerals designate corresponding structure throughout the views.

Figure 2:
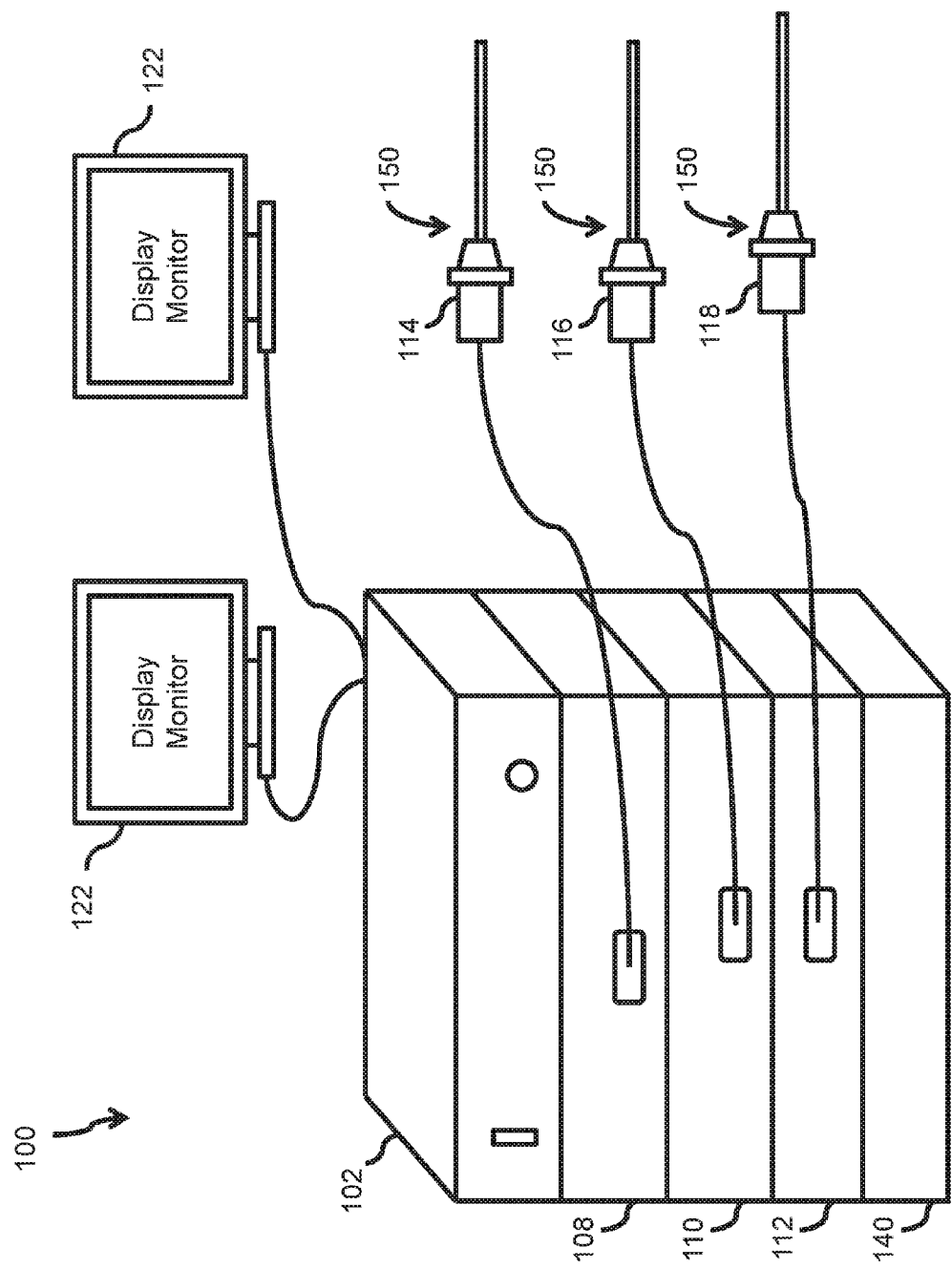
FIG. 2 is perspective diagram of the image capturing system according to FIG. 1.

FIGS. 1-2 depict an exemplary embodiment of an image capturing system 100 acquiring and enhancing image data from one or more camera heads 114, 116, 118. The system 100 includes a control module 102 having a processor 104 that is adapted to provide white balance control of the image signals generated by the camera heads. The processor 104 may be configured as a microprocessor. In some embodiments, the processor 104 comprises a highly-integrated, programmable video processor. In other embodiments, the processor 104 may comprise a graphics processing unit. The control module 102 further has a single white balance control switch 106, which, when engaged, begins a process of white balance calibrating one or more of the camera heads 114, 116, 118. The control switch 106 may be formed as a push-button mounted on a front panel of the control module 102 (see FIG. 2). However, in some embodiments, the control switch 106 may be integrated into a display monitor providing a touch screen interface that is responsive to a touch by a user, i.e., medical professional. Additionally, in some embodiments, the control switch 106 may comprise a control button on a keyboard 126 coupled to the control module 102. The control switch 106 may also be embodied as a voice command device integrated within the control module 106, wherein the voice command device is adapted to initiate and control white balance calibration via means of a user's voice (i.e., verbal commands). With a voice command device, the user can easily operate the system 100 while performing other tasks, such as holding one or more cameras in front of a white surface in preparation of calibrating the cameras. The voice command device can be speaker-independent, and thus can respond to multiple voices regardless of accents. The voice command device may also respond to several commands at once, separating vocal messages, and providing appropriate feedback to properly interpret the multiple commands. In some embodiments, the control module 102 replaces the "physical button" control switch 106 with a "voice command" control switch 106. Alternatively, the control module 102 may be adapted to include both a "physical button" control switch 106 disposed on the front panel thereof as well as a "voice command" control switch. In other embodiments, the white balance control switch 106 may comprise a display monitor coupled to the control module 102, wherein the display monitor provides a gesture-based interface adapted to detect and recognize a plurality of gestures, each gesture being assigned to start a particular function of the control module 102 (e.g., initiate white balance calibration). With a gesture-based interface control switch 106, the system 100 is configured to communicate with the user and enables the user to interact naturally with the system without any mechanical pointing device, such as a mouse. In some embodiments, the control module 102 is adapted with one or more of the above configurations of the control switch 106.

The system 100 includes one or more input modules 108, 110, 112 releasably coupled to the control module 102, wherein the input modules each possess color balance functionality for color correcting and calibrating the color balance of the camera heads connected to the input modules. The input modules may comprise a controller and/or processor programmed to perform the white balance calibration as well as additional image processing functions (discussed in further detail below). In addition, one or more auxiliary input modules 140 may be releasably coupled to the control module 102. The auxiliary input module 140 serves as a compatibility interface having connection ports (e.g., 3G SDI, DVI, s-video, VGA) for connecting various auxiliary devices 142. The auxiliary devices 142 provide existing sources of video and may comprise legacy camera heads, room cameras, PCs, 3G SDI source, and existing CCU systems. Accordingly, the auxiliary device 142 provides the necessary signal conversion and formatting for the auxiliary devices 142 to readily communicate with the control module 102.

It is noted that although FIG. 1 shows the image capturing system 100 having three input modules, as few as one input module may be connected to the control module 102. As a result of the modular architecture of the system 100, the control module 102 can readily support multiple input modules and auxiliary input modules. Different input modules can easily be coupled to and decoupled from the control module 102.

The input modules 108, 110, 112 are coupled to the control module 102 via transmission cables or data links 132. In preferred embodiments, the transmission cables 132 comprise inter-module links which provide duplex (bi-directional) communication between the control module 102 and each input module. The transmission cables 132 may be adapted to transfer electricity to the input modules, wherein the electricity is used to power the input modules and is further transmitted to the camera heads 114, 116, 118 coupled to the input modules 108, 110, 112, respectively. In other embodiments, the input modules receive electrical power via a direct connection to a power supply or electrical outlet. Regardless of whether electrical power is supplied indirectly from the control module 102 or directly from an electrical outlet, the control module 102 regulates and controls the power (e.g., power rating, current rating, voltage rating) supplied to the input modules. The transmission cables 132 may also be designed to transmit illumination derived from a light source 128 coupled to the control module 102.

Each input module 108, 110, 112 includes one or more interface ports, wherein at least one camera head 114, 116, 118 is coupleable with the input modules 108, 110, 112, respectively. The camera heads may be connected via digital or analog conduits designed to transmit images and video to the input modules. These conduits may also be adapted to supply electrical power from the input modules to each individual camera at the proper power ratings. In some embodiments, the camera heads 114, 116, 118 are releasably connected to endoscopes, cystoscopes, or other endoscopic instruments 150 (see FIG. 2). In other embodiments, the camera heads 114, 116, 118 are integrated within and as part of the endoscopic instruments 150. For example, the camera head may be a distal image sensor disposed at the distal end of the shaft of the endoscope 150.

Referring still to FIG. 1, the processor 104 of the control module 102 is configured to centrally and collectively control the white balance calibration functionalities of each input module 108, 110, 112. In addition to providing white balance control, the control module 102 and its processor 104, provide general imaging functions that are not specific to any type of camera head or family of camera heads. Such general imaging functions include signal processing, digital image processing, optical and analog image processing, encoding, transcoding, and other forms of data conversion. The control module 102 may also have an image/video latency adjustment function to synchronize two or more image signals being received from the input modules/camera heads.

The processor 104 is also adapted to provide image enhancements, image restorations, and image compression (e.g., JPEG stills, MPEG clips). The different image enhancements include sharpening of image features and contrast manipulation to make a graphical display more useful for analysis. The processor 104 provides noise reduction, edge crisping and sharpening, filtering, interpolation and magnification (i.e., zoom in, zoom out). A picture-in-picture (PIP) feature is also included to enable the simultaneous display of two or more live images captured by the camera heads coupled to the system 100 or the simultaneous display of a live image feed from a particular camera head as well as data relating to that camera and/or the image signal generated by the camera (e.g., white balance requirements, white balance calibration settings, type/make of camera) The control module 102 supports a fully-featured PIP including side by side, swap, mirror top-bottom and various size arrangements. The processor 104 is also adapted to overlay a graphical user interface while displaying the one or more image signals generated by the cameras and transmitted to the control module 102. Other features built into the processor 104 include still image capturing and video recording. The processor 104 also offers video streaming over a network connection, i.e., Internet, LAN, WAN, for remote viewing of the images captured by the cameras 114, 116, 118.

Each input module 108, 110, 112 is particularly adapted to be compatible with a group or family of camera heads. For instance, an input module may be adapted to work readily with camera heads having the same make and/or model. The input modules may be configured to work with camera heads having the same image sensor technology or imaging architecture. Unlike the control module 102, the input modules provide all functions necessary to support the specific family of camera heads and their associated processing requirements. The input modules are adapted to properly process and encode (and/or transcode) image signals generated by the cameras for transmission to the processor 104. More specifically, the input modules can correctly convert the image signals in proper data format that can be interpreted and analyzed by the processor 104 of the control module 102. In addition, the input modules 108, 110, 112 provide color balance calibration of the camera heads 114, 116, 118, respectively, and more specifically the image signals generated by the camera heads. Each input module is adapted to meet the white balance calibration requirements of the camera head(s) coupled thereto. Accordingly, the input modules function as an interface providing compatibility between families of camera heads and the control module 102.

One example of an input module is a video endoscope "wide mouth" input module. Such an input module may accommodate CCD-based video endoscopes (e.g., ⅛" CCD, 1/10" CCD); CMOS-based imaging devices; or high-definition ("HD") imagers such as 720p60 digital proximal camera heads. The video endoscope input module may serve to accommodate later developed camera control units. Another example of an input module includes an H3-X input module which provides compatibility between the control module and 3-chip high-definition CCD based imaging devices (e.g., H3, H3z, and other H3z-based HD camera heads). Still, another example of an input module includes a digital 1080p input module, which provides the necessary interface between the control module and 1080p60 3-chip proximal camera heads and 1080p60 1-chip proximal camera heads. Other input modules may be adapted to handle future imagers or imaging technologies, including 3D imaging, advanced fluorescence imaging, solid-state variable direction of view endoscopes, and wireless camera heads. The above examples of input modules are merely exemplary, and the image capturing system 100 according to the present invention should not be interpreted as being limited to these specific examples.

The camera heads 114, 116, 118 coupled to the input modules of the image capturing system 100 may comprise different imaging technology (e.g., different image sensors) and/or light source technology. For example, one camera head may comprise of conventional white light imaging while another camera head may comprise of photodynamic diagnostic (PDD) imaging. PDD imaging is different from white light imaging in that PDD utilizes a blue light to provide detailed visualization and detection of malignant tissue. A camera head may incorporate fluorescent imaging (e.g., autofluorescence), which requires a powerful light source, especially in the blue spectral range. Still further, the camera heads, individually, may have multi-spectral imaging capability, and thus provide either wide band imaging (imaging using a light source associated with a wide spectrum of electromagnetic radiation) or narrow band imaging (imaging using a light source associated with a narrow spectrum of electromagnetic radiation) depending on its configuration. Narrow band imaging, in particular, utilizes light of specific blue and green wavelengths to detect more details in a given image.

Due to the different imaging and light source technology, each camera may have distinct white balance calibration requirements. In particular, camera heads which incorporate normal white light require different white balance calibration as compared to camera heads which utilize blue light. Color balance—which is a process of removing unrealistic color casts, so that objects which appear white in person are rendered white in the generated image—require that "color temperature" of the camera's light source be taken into account. A typical temperature range within which conventional white balance and color correction/compensation may be accomplished is 1,000K to 7,500K. This range is sufficient to accurately calibrate the color intensities of an image signal generated by a camera using normal "white light" imaging. However, this range may not be adequate to detect the color temperature of a blue light source and calibrate color intensities to achieve accurate color fidelity for the image signal generated by a camera using "blue light" imaging. An extended temperature range having an increased upper limit must be used to accommodate for "blue light" imaging camera heads. For example, a temperature range of 1,000K to 10,000K or a temperature range of 1,000K to 15,000K may be sufficient to properly white balance a camera head having blue light imaging technology. In other examples, an adjusted temperature range between 1,000K and 20,000K may be needed to ensure comprehensive white balance coverage for all types of "blue light" imaging technology.

In view of the above, it is needed that the image capturing system 100 be able to accommodate white balance compensation for both normal "white light" imaging camera heads and "blue light" imaging camera heads. In other words, a dual white balance capability, and more specifically, a capability of calibrating dual white balance of multiple camera heads, especially camera heads having multi-spectral imaging capability is needed since conventional CCUs and imaging systems fail to provide this functionality.

In particular, the image capturing system 100 is adapted to perform calibration of dual white balance of camera heads 114, 116, 118 upon engaging the white balance control switch 106 disposed on the control module 102, or upon engaging a white balance control switch via a keyboard 126 (or via touch screen monitor, voice command device, or gesture-based interface monitor). The control module 102 detects which input modules 114, 116, 118 are active. An active input module is an input module which is powered on and has at least one active camera (e.g., powered, functional) generating an image signal. Once the input module 102 determines the active input modules that are present, it prompts the user to select a specific camera/input module combination from among the active input modules to dual white balance. Based on user feedback, the control module 102 controls the selected active input module to calibrate white balance of the corresponding active camera. For example, upon initiating white balance control, if camera heads 114, 116 are active while camera head 118 remains inactive, the control module 102 will identify the input modules 108, 110 as being active and request user selection of which active input module/camera combination to calibrate. In some embodiments, the user can make a selection by engaging any head button disposed on the camera head to be calibrated, which provides an indication to the corresponding active input module and control module that this particular camera requires calibration. In other embodiments, the control module 102 may be adapted with a contextual button (e.g., touch screen buttons or keyboard buttons which indicate each of the active input modules) through which the user can select the camera head to calibrate.

Once an active input module is selected, the selected input module (the input module connected to the selected camera) retrieves information regarding the type or make of the selected camera and the light source being used (e.g., white light, blue light). Based on this information, the selected input module conducts proper dual white balance of the active camera coupled to the selected input module and thereby the image signal generated by that active camera. In continuing the above example, if the active camera head 114 is selected by engaging a head button on the camera, the "selected" input module 108 detects this engagement and subsequently retrieves camera information which indicates the type of imaging/light source technology the camera head 114 possesses (for example, blue light PDD). The selected input module 108 then knows to utilize an extended color temperature range and execute any necessary filtering (or conversely remove certain filtering) to achieve proper color balance and accurate color intensities of the image signal generated by the camera head 114. The calibrated image signal is then processed, encoded, and prepared for transmission from the input module 108 to the control module 102 for display. It is noted that when the selected input module performs the white balance calibration, the selected camera head needs to be directed towards a "baseline" white surface for accurate color fidelity to be achieved.

In view of the above, each input module is adapted to provide dual white balance calibration; that is, the input module is able to calibrate equally a camera configured for wide band imaging or the same camera configured for narrow band imaging. By holding a particular camera head configured for wide band imaging and directing its objective lens and "white" light source towards a designated "baseline" white surface (e.g., white gauze, white card), the input module can detect and determine the color temperature (in Kelvins) of the camera's light source. Using this data and the information regarding the baseline "white," the input module manipulates the image signal generated by the camera head in order provide more accurate color intensities. Alternatively, if the camera head is configured for narrow band imaging and, therefore, is adapted with a "blue" light source, the input module is capable of using an extended temperature range necessary to properly detect and determine the color temperature of the blue light source and manipulate the image signal to provide more accurate color intensities. The input modules, therefore, are capable of providing a dual white balance calibration for both lights sources, such that each type of light source may be calibrated correctly for white balance.

The white balance calibration process performed by the input modules may comprise a plurality of color temperature filters which assist in remapping color values to simulate variations in color temperature of the camera head's light source. In addition to performing the necessary color filtering, the white balance calibration process may also include neutral-density filtering, black level trim for RGB components, gain trim for RGB components and master gain modification to the image signals to achieve color fidelity.

Since the system 100 is adapted to provide dual white balance capabilities, the input modules 108, 110, 112 can use either the typical white light color temperature range or an extended color temperature range for blue light in order to provide proper color correction. Nevertheless, the input modules 108, 110, 112 are each adapted to provide a warning when color correction fails, and accurate, true color intensities cannot be achieved. For example, if the color temperature of the light source of the camera head exceeds the white balance control range, the associated input module issues a warning to the control module, which then provides a visual and/or audible warning of the calibration failure.

The system 100 also provides feedback as to the correct performance of white balance. The system indicates failures when either the field of view of the camera head is too dark or too bright to properly white balance configure the camera head. Generally, when the field of view is too dark, the system informs the user that the distance between the endoscope—and more specifically the imaging unit disposed therein—and the white surface must be shortened before repeating white balance. In contrast, when the field of view is too bright, the system recommends that the distance between the endoscope and the white surface be extended before initiating another white balance process.

In some embodiments, when the white balance process is successfully completed, the control module 102 locks or deactivates any white balance head buttons on the calibrated camera. For example, after the camera head 114 is color corrected for dual white balance by the input module 108, the control module 102 deactivates any white balance head buttons disposed on the camera head 114, thereby making them "non-selectable." As such, if any white balance head button of the camera head 114 is selected or engaged by the medical professional, the control module 102 ignores the button engagement and prevents any white balancing to be conducted on the camera head 114. In other embodiments, the imaging system 100, at all times, locks or deactivates any white balance head buttons on all the camera heads. Accordingly, the only way to perform a white balance on any of the cameras coupled to the system is by engagement of the white balance control switch 106 on the control module 102, via a control switch on keyboard 126, via a control switch incorporated into a touch screen display, via a control switch integrated into a voice command device, or via a control switch implemented into a gesture-based interface. This locking feature/mechanism helps to prevent, or at least reduces the likelihood that, an accidental or unintentional engagement of a white balance head button recalibrates the camera head 114 such that the image signals generated therefrom have inaccurate color fidelity. Therefore, this feature also eliminates any downtime associated with having to remove the endoscopic instrument 150 coupled with the camera 114 from an incision or natural body opening through which the endoscopic instrument 150 is inserted, recalibrate the camera head's white balance, and carefully—without causing additional tissue injury—guide the endoscopic instrument back through the incision or natural body opening. The locking feature is an advantageous feature which ensures that a proper white balance calibration setting is maintained throughout a given medical procedure.

In some embodiments, each input module 108, 110, 112 has a storage unit for saving the camera information retrieved from the cameras 114, 116, 118 as well as the white balance settings after calibration has been completed on the cameras. The saved calibration settings may be used, in certain situations, in order to quickly and reliably dual white balance the camera and its image signal. For example, the image capturing system 100 is configured such that, if a selected input module (which has calibrated a camera coupled thereto) is disconnected and subsequently reconnected to the control module 102, the control module controls this particular input module to calibrate white balance based on calibration settings saved in the storage unit. This provides for a quick and reliable form of dual white balance calibration and further ensures that the temporary disconnection does not affect the image quality due to any inadvertent change in calibration settings.

There may be situations where the medical professional requires the use of more than one camera in a medical procedure. In order to dual white balance additional cameras after an initial calibration of a first camera, the white balance control switch 106 on the control module 102, or the control switch on keyboard 126 coupled to the control module 102 (or a control switch incorporated into a touch screen display, voice command device, or gesture-based interface), must be re-engaged. Thereafter, the medical professional merely repeats the above steps and selects the additional cameras to be dual white balanced. For example, if use of both active cameras 114, 116 is required in a medical procedure, the medical professional may first calibrate camera head 114 as previously discussed. Once camera 114 has been color corrected, the medical professional can re-engage the control switch 106 on the control module, or on the keyboard 126, and, upon being prompted by the control module 102 to select a camera head to calibrate, engage any of the head buttons disposed on the camera head 116. Thereafter, the input module 110 and control module 102 detect that camera head 116 has been selected for calibration. The "selected" input module 110 begins retrieving camera information indicating the type of light source technology camera head 116 is currently configured for, such as normal white light imaging. As a result, the selected input module 110 knows that a typical white light color temperature range may be used for dual white balance calibration purposes.

In some embodiments, where at least two active cameras require calibration, the control module 102 controls the associated active input modules, such as input modules 108, 110, to calibrate white balance of the image signals generated by the active cameras 114, 116, so that the image signals have matching color fidelity. In other words, the image captured by camera 114 appears the same with respect to color balance and color intensities compared to the image captured by camera 116. It is important that matching color balance is achieved so that the medical professional has consistent views of a given bodily structure to make a proper and informed diagnosis.

There may also be situations where the medical professional, having calibrated one or more cameras prior to the start of a medical procedure, realizes during the procedure that he/she needs to use an inactive camera. The system 100 may be adapted such that when the inactive camera is activated, the control module 102 detects the newly activated camera. The control module 102 subsequently controls the input module coupled to the newly activated camera to calibrate dual white balance of the image signal being generated by the newly activated camera. In particular, the control module 102 may adjust the white balance of the image signal generated by the newly activated camera such that it has matching color fidelity as the image signals of previously calibrated input module/camera combinations. In some embodiments, the newly activated camera may be white balanced by engaging the control switch 106 on the control module, or via keyboard 126 (or via touch screen monitor, voice command device, or gesture-based interface monitor). This feature of the system 100 helps to ensure that a consistent color balance is provided by all cameras being used by the medical professional.

In some embodiments, in addition to calibrating white balance of the camera heads 114, 116, 118, the input modules 108, 110, 112 are also adapted to adjust hue and saturation of the image signals generated by the active camera heads. By also adjusting hue and saturation, true color fidelity is achieved in each calibrated camera and matching color fidelity among multiple image signals may further be achieved.

The system 100 also provides for manual adjustment of white balance calibration of the cameras. In particular, with manual white balance adjustment, the medical professional is able to fine-tune the dual white balance calibration settings to his/her preferences. The user may adjust the red, green, and/or blue components of an image signal in order to obtain a color balance that meets the user's preferences.

The control module 102 is also adapted with a time-out period (after engaging the control switch 106 on the control module 102, or a control switch on the keyboard 126), wherein if no user feedback is provided upon being prompted for selection of an active input module/camera combination to dual white balance, the white balance control process terminates. As such, no color correction or calibration is performed by the system 100.

The image capturing system 100 may further be arranged such that at least one display monitor/recorder 122 is coupleable to the control module 102. For example, a DVI monitor/recorder or 3G SDI monitor/recorder may be connected to the control module for displaying the calibrated image signals provided by any of the input modules. As previously mentioned, the control module 102 may perform further image enhancements to the calibrated signals before being displayed on the display monitors 122 (e.g., contrast adjustment, PIP formatting, GUI overlay).

In some embodiments, one or more input/output (I/O) devices 126 may be coupleable to the control module 102. For example, an external storage unit (e.g., external hard drive) may be coupled to the control module 102 to save the calibrated image signals as well as the actual formatted display as viewed on the display monitor 122. The storage unit may further be adapted to save the calibration settings of each of the camera heads that are calibrated by the input modules. The I/O device 126 may comprise a printer, which allows for real-time printing of image stills (e.g., JPEGs). In other embodiments, the I/O device 126 comprises a keyboard or keypad, which functions as an input mechanism and allows the user to enter in different data into the system 100. Other I/O devices 126 which may be coupled to the control module 102 include port adapters and ACC/USB connectable devices.

Figure 3:
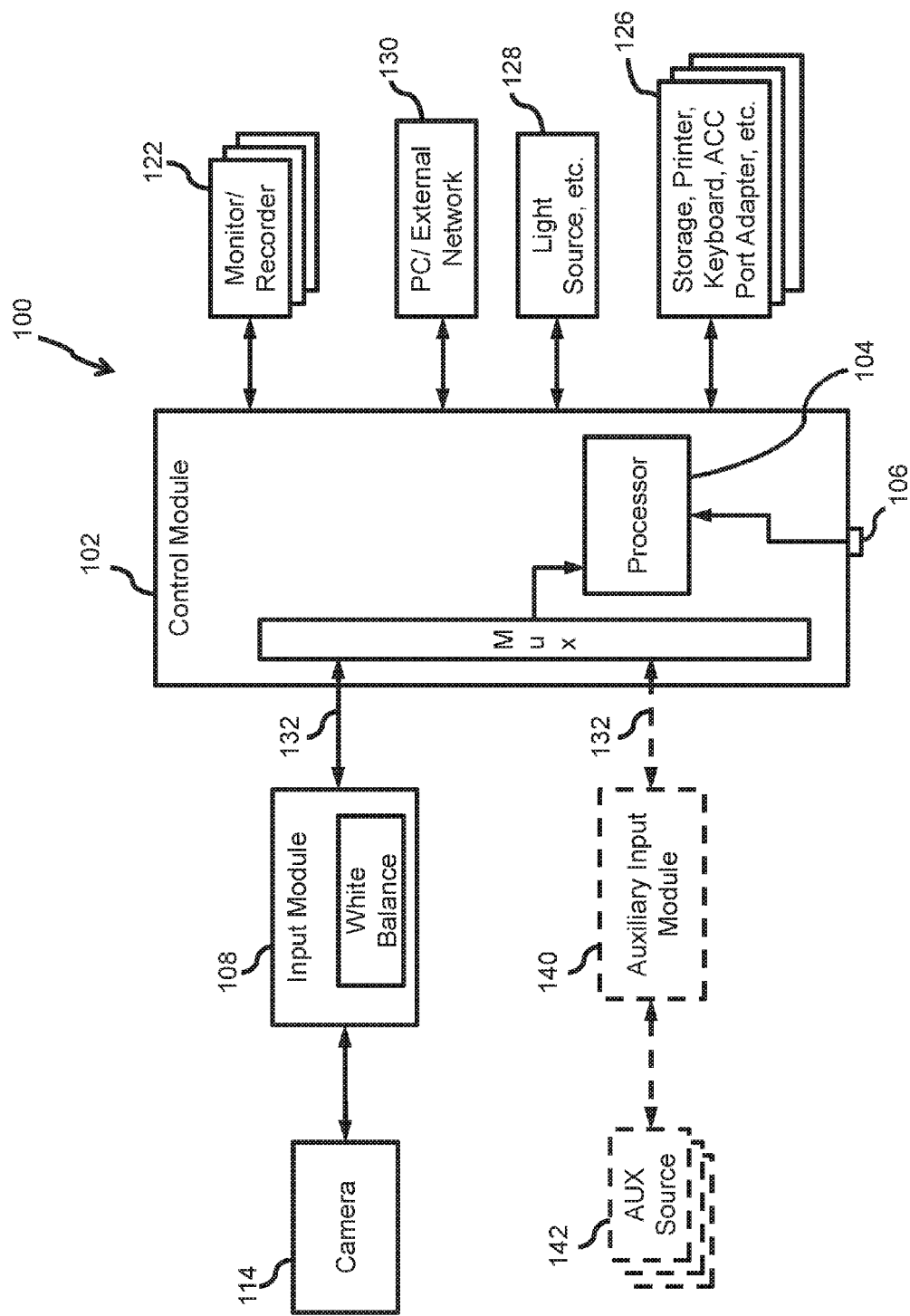
FIG. 3 is a block diagram of an embodiment of the image capturing system of FIG. 1.

Referring to FIG. 3, another embodiment of the image capturing system 100 is shown. In particular, the image capturing system 100 includes a control module 102 and only one input module 108 releasably coupled to the control module 102. The control module 102 has a white balance control switch 106 and a processor 104 which provides white balance control of the input module 108. The white balance control of the processor 104 is adapted to control the white balance calibration function of the input module 108. A single multi-spectral imaging camera 114 is coupled to the input module 108.

An auxiliary input module 140 may be connected to the control module 102 to provide a communication interface between auxiliary devices 142 (e.g., legacy camera heads, room cameras, PCs, 3G SDI source, and existing CCU systems) and the control module 102. The auxiliary module 140 is designed to provide any necessary data format conversion so that communication to and from the auxiliary devices may be established without the need for additional hardware and/or software.

To initiate white balance control in the system 100 as shown in FIG. 3, a user engages the white balance control switch 106 on the control module 102, or engages a control switch on a keyboard 126 coupled to control module 102 (or via touch screen monitor, voice command device, or gesture-based interface monitor). The control module detects which available input modules are active. With only one input module 108 and one multi-spectral imaging camera 114 present in the system 100, the control module 102 automatically determines that this input module/camera combination is an active input module and further is the "selected" input module to be calibrated. Accordingly, the control module 102 need not and does not prompt the user to select the particular camera head to white balance calibrate. Instead, the control module 102 automatically instructs the input module 108 to perform dual white balance calibration. In order to ensure that the multi-spectral camera 114 is properly calibrated, the input module 108 retrieves camera information regarding the type or make of the camera 114 as well as the current configuration of the camera with respect to imaging/light source. The input module 108 is able to analyze the settings and configurations of the camera 114 and ascertain if the camera is arranged for wide band imaging ("white light" imaging) or narrow band imaging ("blue light" imaging). Based on the camera information obtained by the input module 108, the correct color temperature range is used to properly color correct the image signal generated by the camera 114. If the camera 114 is set for wide band imaging, the input module 108 will utilize the typical white light color temperature range (i.e., 1,000K to 7,500K) to dual white balance the image signal. Alternatively, if the camera 114 is set for narrow band imaging, the input module 108 uses an extended color temperature range adapted to correctly recognize and color compensate the blue light source.

The input module 108 is also adapted to adjust hue and saturation levels to further correct the color balance of the image signal generated by the camera 114.

After the input module 108 completes dual white balance calibration, the calibrated image signal is subsequently processed, encoded, and prepared for transmission to the control module 102 for display on one or more display monitors 122.

FIG. 4 shows a method of white balancing image date generated by a camera (e.g., multi-spectral camera) and captured by the image capturing system 100 of FIG. 1. The method comprises the steps of: providing a control module and at least one input module of the image capturing system, wherein the control module has a processor adapted for white balance control and a control switch adapted to initiate white balance control, connecting the at least one input module to the control module, and connecting at least one camera to one of the at least one input module, wherein the at least one camera is compatible with the one input module. The method of white balancing further comprises the steps of: engaging a white balance control switch 302, detecting, via the control module, at least one active input module 304, 306, wherein the active input module has at least one active camera coupled thereto, the active camera generating an image signal, and selecting one of the at least one active camera for calibration 308, 310. More specifically, the step of detecting at least one active input module comprises the steps of: detecting the number of input modules coupled to the control module and the number of cameras coupled to the input modules 304. If there is only one input module coupled to the control module and one camera coupled to the input module (such as shown in FIG. 3), then the following steps are performed: automatic white balance calibrating the image signal generated by the one camera 312 and transmitting the calibrated image signal for display on a display monitor 314. If there is more than one camera coupled to the image capturing system, then the control module detects, from among the number of input modules and cameras physically connected to the system, the number of active input modules and active cameras. If there is only one active camera (i.e., powered and functional camera) from among the multiple cameras coupled to the system, then the step of white balance calibrating the image signal generated by the one camera 312 and transmitting the calibrated image signal for display on a display monitor 314 are performed. If the number of active cameras is greater than one, then the method of white balancing comprises the step of selecting one active camera to calibrate 308, 310. This step of selecting, in particular, includes the steps of prompting selection of one active camera to be calibrated 308 and determining whether a selection is made within a time-out period 310 (e.g., 10 seconds). If a selection is not made within the time-out period, the control module will stop white balance control and calibration 320. If selection is made within the time-out period, the method of white balancing further comprises the steps of: controlling, via the control module, the active input module coupled to the selected camera to calibrate the image signal of the selected camera 312, and transmitting the calibrated image signal to the control module for display 314.

In some embodiments, the step of selecting a particular camera to be calibrated 310 further comprises the steps of: aiming the camera at a white surface such that the objective lens of the camera is proximate to the white surface, and engaging any head button on the camera to transmit an identification signal to the control module, wherein the identification signal indicates that this particular camera requires white balance calibration.

In some embodiments, the step of controlling the active input module coupled to the selected camera to calibrate dual white balance of the image signal of the selected camera 312 also comprises the steps of: retrieving, via the active input module coupled to the selected camera, camera information from the selected camera, wherein the camera information includes information regarding the imaging and light source configuration of the selected camera, and configuring the active input module coupled to the selected camera based on the camera information in order to provide a white balance calibration adapted to the selected camera.

Moreover, in some embodiments, the step of transmitting the calibrated image signal 314 further comprises the steps of: processing the calibrated image signal via the active input module that is coupled to the selected camera, and converting the calibrated image signal into a data format that may be interpreted and analyzed by said control module.

While the invention has been specifically described in connection with certain specific embodiments thereof, it is to be understood that this is by way of illustration and not of limitation, and that various changes and modifications in form and details may be made thereto, and the scope of the appended claims should be construed as broadly as the prior art will permit.

The description of the invention is merely exemplary in nature, and, thus, variations that do not depart from the gist of the invention are intended to be within the scope of the invention. Such variations are not to be regarded as a departure from the spirit and scope of the invention.

What is claimed is:

1. A system for capturing image data, said system comprising:
   a control module having a control switch and a processor, said processor being configured for white balance control and said control switch being configured to initiate white balance control;
   at least one input module connected to said control module, said input module configured to provide white balance calibration for wide band imaging and narrow band imaging;
   at least one camera coupled to said at least one input module such that said at least one input module is connected between said at least one camera and said control module;
   one or more of said at least one input module configured as active input modules, each active input module having an active camera generating an image signal; and
   said control module detecting said one or more active input modules and controlling one of said one or more active input modules, selected based on user feedback, to retrieve a camera setting indicative of whether wide band imaging or narrow band imaging is being used by the active camera of the selected input module, to provide dual white balance calibration of the image signal of the active camera coupled to the selected input module based on the camera setting, and to transmit the calibrated image signal to said control module for display.

2. The system of claim 1, wherein said control module deactivates white balance initiation via said active camera so that calibration of the image signals of the active camera is initiated via said control switch only.

3. The system of claim 2, further comprising a keyboard coupled to said control module, wherein said control switch comprises a button on said keyboard.

4. The system of claim 2, wherein said control switch comprises a voice command device integrated with said control module, said voice command device being adapted to receive verbal commands.

5. The system of claim 2, wherein said control switch comprises a touch screen monitor, said touch screen monitor providing a touch screen interface to initiate white balance control.

6. The system of claim 5, wherein said touch screen monitor provides a gesture-based interface, wherein said gesture-based interface detects gestures for controlling said control module.

7. The system of claim 1, wherein said camera setting comprises imaging configuration data of said active camera coupled to said selected input module.

8. The system of claim 1, wherein, when only one input module is connected to said control module and one camera is connected to said one input module, said control module automatically controls said one input module to calibrate white balance of the image signal of said camera and to transmit the calibrated image signal to said control module for display.

9. The system of claim 1, wherein said control module detects at least two active input modules, each active input module having at least one active camera coupled thereto; and
  wherein said control module controls at least two active input modules, selected based on user feedback, to calibrate white balance of the image signals of said selected input modules to have matching color fidelity.

10. The system of claim 9, wherein said selected input modules are adapted to adjust hue and saturation of the image signals transmitted to said selected input modules so that said image signals have matching color fidelity.

11. The system of claim 1, wherein, when a camera is activated, said control module detects said newly activated camera, controls said input module connected to said newly activated camera to calibrate white balance of an image signal of said newly activated camera, and adjusts the white balance of said image signal of said newly activated camera so that said newly activated camera has matching color fidelity as the image signal of said selected input module.

12. The system of claim 1, wherein said one or more active input modules are adapted to process and encode the image signals of said active cameras for transmission to said processor.

13. The system of claim 1, wherein at least one display monitor is coupleable to said control module, said display monitor displaying said calibrated image signal transmitted from said selected input module to said control module.

14. The system of claim 1, wherein said at least one input module comprises a storage unit, said storage unit being adapted to save calibration settings of the at least one camera coupled to said input module.

15. The system of claim 14, wherein said control module is adapted to use the calibration settings saved in the storage unit of said selected input module to calibrate the white balance of said image signal of said active camera coupled to said selected input module.

16. The system of claim 15, wherein, when the selected input module is disconnected and reconnected to said control module, said control module uses the calibration settings saved in the storage unit of said selected input module to adjust the white balance of the active camera coupled to said selected input module.

17. The system of claim 14, wherein said at least one input module is adapted to retrieve camera information of said camera coupled to said at least one input module, said camera information including imaging configuration data of said camera; and
  wherein said camera information is saved in said storage unit.

18. The system of claim 1, wherein said control module provides for manual adjustment of white balance calibration of the image signal of the active camera coupled to said selected input module.

19. A system for capturing image data, said system comprising:
  a control module having a control switch and a processor, said processor being configured for white balance control and said control switch being configured to initiate white balance control;
  a plurality of input modules connected to said control module and communicating with said processor, each input module being compatible with a family of cameras where all cameras of the family have a common imaging architecture, at least one of said input modules being configured to provide white balance calibration for wide band imaging and narrow band imaging;
  at least one camera coupled to each of said input modules such that each input module is connected between said respective at least one camera and said control module, each input module being configured to provide white balance calibration for said at least one camera coupled thereto;
  two or more of said plurality of input modules configured as active input modules, each active input module having at least one active camera generating an image signal; and
  said control module detecting said two or more active input modules, said control module being configured to receive user feedback selecting one of the active cameras of said two or more active input modules to be dual white balanced, and said control module controlling the active input module coupled to said selected camera to retrieve a camera setting indicative of whether wide band imaging or narrow band imaging is being used by the selected camera, to calibrate dual white balance of the image signal of the selected camera based on the camera setting, and to transmit the calibrated image signal to said control module for display.

20. The system of claim 19, wherein said control module deactivates white balance initiation via said active cameras so that calibration of the image signals of said active cameras coupled to said active image modules are initiated via said control switch only.

21. The system of claim 19, wherein said control module is adapted to receive user feedback selecting at least two of said active cameras coupled to said active input modules, said control module controlling the active input modules coupled with the selected cameras to calibrate dual white balance of the image signals of the selected cameras.

22. The system of claim 21, wherein the image signals of the selected cameras are calibrated to have matching color fidelity.

23. The system of claim 21, wherein said control module controls said active input modules coupled with said selected cameras to sequentially calibrate dual white balance of the image signals of said selected cameras.

24. The system of claim 19, wherein said active input modules are adapted to process and encode the image signals of said active cameras for transmission to said processor.

25. The system of claim 19, further comprising at least one display monitor coupled to said control module, said at least one display monitor displaying at least said calibrated image signal that is transmitted to said control module.

26. The system of claim 19, wherein said control module is adapted to process said calibrated image signal received from said selected camera and provide image enhancements.

27. The system of claim 26, wherein said image enhancements comprises zoom, picture-in-picture, and graphical user interface overlay.

28. The system of claim 19, wherein said control module is adapted to connect to a network and stream said calibrated image signal through said network.

29. A system for capturing image data, said system comprising:
- a control module having a control switch and a processor, said processor being configured for white balance control and said control switch being configured to initiate white balance control;
- at least one input module connected to said control module, said input module configured to provide white balance calibration for wide band imaging and narrow band imaging;
- at least one camera coupled to said at least one input module such that said at least one input module is connected between said at least one camera and said control module; and
- at least one display monitor coupled to said control module;
- one or more of said at least one input module configured as active input modules, each active input module having an active camera generating an image signal; and
- said control module detecting said one or more active input modules and controlling one of said one or more active input modules, selected based on user feedback, to retrieve a camera setting indicative of whether wide band imaging or narrow band imaging is being used by the active camera of the selected input module, to provide dual white balance calibration of the image signal of the active camera coupled to the selected input module based on the camera setting, and to transmit the calibrated image signal to said control module for display on said display monitor.

30. A method for white balancing image data captured by an image capturing system in a medical operating room, said method comprising the steps of:
- providing a control module and at least one input module of said image capturing system, said control module having a processor configured for white balance control and a control switch configured to initiate white balance control, said input module configured to provide white balance calibration for wide band imaging and narrow band imaging;
- connecting the at least one input module to the control module;
- coupling at least one camera to one of said at least one input module such that said at least one input module is connected between said at least one camera and said control module;
- engaging said control switch of said control module;
- detecting, via said control module, at least one active input module from said at least one input module, said active input module having at least one active camera coupled thereto, said active camera generating an image signal;
- selecting one of said at least one active camera for calibration; and
- controlling, via said control module, the active input module coupled to the selected camera to retrieve a camera setting indicative of whether wide band imaging or narrow band imaging is being used by the selected camera and to calibrate dual white balance of the image signal of said selected camera based on the camera setting; and
- transmitting said calibrated image signal to said control module for display on a display monitor.

31. A method of claim 30, wherein said step of selecting one of said at least one active camera for calibration further comprises:
- aiming said camera at a white surface such that an objective lens of said camera is proximate to said white surface; and
- engaging one head button disposed on said camera to transmit an identification signal to said control module, said identification signal indicating that said camera requires white balance calibration.

32. A method of claim 30, wherein said step of controlling the active input module coupled to the selected camera further comprises:
- configuring the active input module coupled to the selected camera based on said camera setting to provide a white balance calibration adapted to the selected camera, wherein said camera setting includes at least one of imaging configuration or light source configuration of said selected camera.

33. A method of claim 30, wherein said step of transmitting said calibrated image signal further comprises:
- processing said calibrated image signal by said active input module that is coupled to said selected camera; and
- converting said calibrated image signal into a data format recognized by said control module.

* * * * *